United States Patent [19]

Maupetit et al.

[11] Patent Number: 4,503,034
[45] Date of Patent: Mar. 5, 1985

[54] PASTE FOR PROTECTING THE SKIN

[75] Inventors: Philippe Maupetit, Aulnay sur Bois; Bernard Demoulin, St. Pee sur Nivelle, both of France

[73] Assignee: Laboratoires Biotrol S.A, Paris, France

[21] Appl. No.: 529,700

[22] Filed: Sep. 2, 1983

[30] Foreign Application Priority Data

Sep. 7, 1982 [FR] France .................. 82 15191

[51] Int. Cl.$^3$ ............................................. A61K 31/79
[52] U.S. Cl. ....................................... 424/80; 514/969
[58] Field of Search .................. 424/80; 604/332, 336

[56] References Cited

U.S. PATENT DOCUMENTS

| | | | |
|---|---|---|---|
| 3,876,771 | 4/1975 | Denner | 424/78 |
| 3,933,766 | 1/1976 | Hoffmann et al. | 260/80.3 R |
| 3,980,084 | 9/1976 | Kross | 604/336 |
| 4,045,550 | 8/1977 | Kelly et al. | 424/70 |
| 4,078,568 | 3/1978 | Etes et al. | 128/283 |
| 4,192,785 | 3/1980 | Chen et al. | 260/17.4 CC |

FOREIGN PATENT DOCUMENTS

WO82/00005 1/1982 PCT Int'l Appl.
WO82/00099 1/1982 PCT Int'l Appl.

*Primary Examiner*—Leonard Schenkman
*Attorney, Agent, or Firm*—Berman, Aisenberg & Platt

[57] ABSTRACT

Paste for protecting the skin, fundamentally comprising:

at least one hydrocolloid, insolubilized carboxymethylcellulose and/or another superabsorbent product derived from hydrocolloids, and a polyvinylpyrrolidone having a molecular weight of the order of 25,000 to 30,000, as thickeners, demineralized water as a binder, and to fix the latter, a suitable oil and a suitable stearate, and also crosslinked and insolubilized polyvinylpyrrolidone, and advantageously sorbitol and/or polyethylene glycol.

Application, in particular, for providing protection against weeping wounds and/or against matter flowing out of stomata from the urinary or digestive tract.

19 Claims, No Drawings

PASTE FOR PROTECTING THE SKIN

BACKGROUND OF THE INVENTION

The present invention relates to products for protecting the skin, in particular against attack by body discharges from weeping wounds (surgical or accident wounds) and/or by matter flowing out of stomata from the urinary or digestive tract, and very particularly to their application as pastes for forming a seal between the stomata and the appliances conventionally used.

In fact, it is important to protect either the skin which can be attacked by weeping surgical or accident wounds, or, around a stoma, the skin in contact with the urine (in the case of a ureterostomy) or with the stools (in the case of a colostomy and an ileostomy). As regards the stomata, they are not in fact all of a perfectly regular shape, and they have deep cavities, which are zones where the skin is not protected by the collecting appliance normally applied thereto.

Furthermore, the collecting appliances made available to patients with stomata have standardized orifice diameters which do not necessarily correspond to the actual size of the stoma to be fitted with the appliance.

Paste already exist on the market which are supposed to be able to act as a barrier to aggressive substances. However, these known pastes have certain disadvantages or prove difficult to use.

Thus, the pastes currently on the market contain an alcohol, a ketone or an ether as the main binder, and for this very reason must be contraindicated for irritated or sensitive skin.

French Pat. Nos. 78/16,326 and 78/16,615 describe adhesive compositions used for sealing stomata, which are based on natural or synthetic polymers but are in the form of discs and are therefore difficult to apply locally.

A paste (which is easy to apply and remove and which, once applied, protects the whole region of skin surrounding the wounds or the stoma against digestive acids and enzymes, alkaline stools, urine and other aggresive matter) having a novel formulation has now been found and developed. Furthermore, this paste has proved compatible with all bandages and all currently known systems for fixing collecting or draining bags (adhesive bags, bags with a Karaya seal and bags with a synthetic seal or support).

The present invention relates firstly to a paste for protecting the skin, which fundamentally comprises:

at least one hydrocolloid and/or another superabsorbent derived from hydrocolloids, insolubilized carboxymethylcellulose and a polyvinylpyrrolidone having a molecular weight of the order of 25,000 to 30,000, in particular as thickeners, demineralized water as a binder, in combination with:
a suitable oil and a suitable stearate, and also
crosslinked and insolubilized polyvinylpyrrolidone, and advantageously,
sorbitol and/or polyethyleneglycol.

In a preferred embodiment, the essential components of the paste are in the following ratios and proportions by weight/weight:

powder/water: 1 to 3.5 approximately, preferably 1.5 to 1.9;

stearate/(water+oil+sorbitol and/or polyethyleneglycol)$\geq$0.10, preferably about 0.15;

PVP/water: 0.5 to 2 approximately; and in another preferred embodiment:

% of PVPP$\leq$3% by weight/weight of the finished paste.

In these ratios, and also in the remainder of the present text, the term "powder" is understood as meaning all the pulverulent components mixed together, namely: the hydrocolloid, the insolubilized carboxymethylcellulose (abbreviated to CMC) and the polyvinylpyrrolidone (abbreviated to PVP); also, PVPP denotes the crosslinked and insolubilized polyvinylpyrrolidone.

A paste corresponding to a formulation of this type has proved exceptionally easy to apply and remove and, once applied to a region of skin containing a wound, or to the periphery of a stoma, is shown to protect, with an efficacy hitherto unknown, the whole of the region of skin surrounding the wound or the stoma against digestive acids and enzymes, alkaline stools, urine and other usual aggressive matter.

More generally, it seems, surprisingly, that a paste of this type can also be used as an inert carrier and/or vehicle for pharmaceutical compositions for the slow percutaneous administration of various active principles acting by transdermic diffusion (also called "transdermic" products). These transdermic products are currently known and used. It is clear that, in this type of application, the paste protects both the skin and the transdermic product itself against any external attack.

Furthermore, because the binding base of the paste is essentially demineralized water (whereas, in all the formulations currently on the market, it seems that the main binding base is an alcohol, a ketone or an ether), the paste according to the invention is not contraindicated for irritated skin as are the paste formulations currently on the market; by contrast, the paste according to the invention comprises a combination of aqueous binding base with oil (such as a paraffin oil or the like), forming an emulsion enabling another component of the formulation, namely the crosslinked and insolubilized polyvinylpyrrolidone, to utilize its film-forming properties which are particularly effective for rejuvenating damaged skin.

Moreover, the insolubilized carboxymethylcellulose (that is to say the carboxymethylcellulose crosslinked or insolubilized in any other way by methods know per se) seems to give the paste an exceptionally large absorption capacity for the moisture and the aqueous effluents discharged from the patient's body. Under the action of the moisture absorbed in this way, it gives the paste a high-viscosity gel texture and gives it the property of being able to change into a barrier impermeable to any external liquid phase, irrespective of the pH.

In addition to the essential or optional components indicated above, the paste according to the invention can also comprise secondary components chosen from amongst the conventional constituents and adjuvants, such as, in particular, preservatives, for example sorbic acid or the sodium salt or methyl para-hydroxybenzoate.

The hydrocolloid or mixture of hydrocolloids present in the paste according to the invention can be appropriately chosen by those skilled in the art from amongst the known hydrocolloids or formulated from several of the latter. These can be hydrocolloids extracted from plants (seeds or algae) or hydrocolloids synthesized by fermentation. Examples of hydrocolloids are guar, carob, alginates and carragheenins. Preference is given to alginates and very particularly to alkali metal alginates (especially sodium alginate), which are excellent thickeners, readily soluble and unlikely to create sealing zones in the medium to be thickened, and, more generally, any superabsorbent product, such as those formulated from hydrocolloids (for example the product marketed under the name Cecalgum by the Ceca Company and produced from alginic acid), can be used for the same purpose, either with the hydrocolloids or in place of them.

The insolubilized carboxymethylcellulose can be, for example, the product marketed under the name Aqualon by the Hercules France Company, which is a superabsorbent component. The polyvinylpyrrolidone having a molecular weight of the order of 25,000 to 30,000 is a very fine powder which, apart from its film-forming, bacteria-inhibiting and adhesive properties, makes it possible, in aqueous solution, to provide the paste with a good fluidity, by virtue of its very high binding capacity. All other things being equal, the proportion of this PVP powder relative to the water seems to have a great influence on the viscosity of the paste; to obtain a paste which is neither too fluid nor too thick, the ratio of PVP/water should in practice be kept between 0.5 and 2 approximately, preferably between 0.6 and 1.25 approximately.

The suitable oil and the suitable stearate and to fix the demineralized water, which is the binder for the paste, can be chosen respectively from amongst:

paraffin oil of Codex grade (France), such as, for example, a vaseline oil, which is in liquid form and emulsifies with the aqueous phase in the paste; and a stearic acid fatty ester, such as, for example, glycol palmitostearate. In particular, glycol palmitostearate in combination with a polyoxyethyleneated fatty alcohol phosphate, which is in the form of a wax, can be used as an acid anionic gelling base for a water/oil mixture; it is a self-emulsifier. However, it is also possible to use other fatty alcohol stearates, such as, for example, the palmitostearate of glycerol and of polyoxyethylene glycol or the palmitostearate of ethylene glycol and of polyethylene glycol.

The crosslinked and insolubilized polyvinylpyrrolidone (PVPP) is a very fine powder having a high chemical inertness, adhesiveness in a moist environment, a high hydrophilicity, insolubility in aqueous media and good film-forming properties.

The paste according to the invention can moreover contain sorbitol and/or polyethylene glycol.

Sorbitol is in powder form; it constitues a binder complement in an aqueous phase and makes it possible, if desired, to reduce the amount of binder, which consists of water. In common practice, it is used in the form of a 70% aqueous solution and the amounts indicated below for the sorbitol correspond to amounts of a sorbitol solution of this type (referred to as aqueous sorbitol). Polyethylene glycol is a product which makes it possible, if desired, to improve the flow properties of the paste while at the same time making it possible to reduce the proportion of paraffin oil. It is in powder form for molecular weights of 4,000 to 6,000 and in liquid form for molecular weights of the order of 400.

If desired, it is possible to use one or other of these optional constituents, or both, the most appropriate grade being chosen in each case.

The respective proportions of the abovementioned constituents can be appropriately chosen by those skilled in the art, who can do this by carrying out routine experiments and can determine whether certain proportions initially suggested on an empirical basis are indeed suitable. In this respect, it is preferable to comply with the ratios of powder/water, stearate/(water+oil/sorbitol) and PVP/water, and also with the proportion of PVPP, which were indicated above as being advantageous. The amounts of each of the individual components are then either unrestricted or governed by these ratios and proportions.

As regards the possible addition of preservatives to this paste, it is preferred to use the pair comprising the sodium salt of methyl p-hydroxybenzoate and sorbic acid, which is a fungicide, of Codex grade (France), making it possible to have synergy at respective doses by weight of 1/1,000 and 0.5/1,000, relative to the weight of the paste. Of course, these preservatives are only mentioned as examples. The choice of preservatives is only governed by their French Codex registration and their intrinsic inhibitory power when they are combinated with the other constituents of the paste.

The process for the manufacture of the paste according to the invention uses techniques known to those skilled in the art; it can consist, for example, of one of the following two procedures:

I (a). The oil, the stearate and the water are mixed and the mixture is heated to about 70° C., with agitation, in order to produce an emulsion.

(b). The PVPP is mixed with the sorbitol or the polyethylene glycol, or both, and, if desired, with preservatives.

(c). Demineralized water is added to the PVP and the mixture is agitated until the PVP has completely dissolved, the temperature being kept below 70° C.; the hydrocolloid and then the CMC are added thereto, with agitation; once the preparation produced in this way is very homogeneous, the temperature is kept below 70° C. and the mixture, resulting from steps a and b are added, with agitation.

II (a). The stearate is heated to 70° C. and mixed with the paraffin oil.

(b). In a separate operation, the sorbitol and, if appropriate, preservatives are added to the PVPP, if desired.

(c). Demineralized water is added to the PVP, with agitation; the hydrocolloid and the CMC are then added successively, still with agitation; the mixture obtained in step b is added to this preparation, the temperature being kept below 70° C., and the product from step a is added, with agitation.

In these procedures, provision may also be made to add polyethylene glycol, either as a replacement for part of the sorbitol or in place of the sorbitol, as desired.

The present invention also relates to the application of the abovementioned pastes for protecting the skin, in particular against attack by weeping wounds and/or by matter flowing out of stomata from the urinary or digestive tract. The primary irritation index of the skin with pastes according to the invention was measured by a commonly used process and the tests showed that the pastes had no irritant activity. They were used to protect stomata of irregular shapes, when there are wrinkles and cracks in the skin such that the adhesives on the usual collecting bags cannot adhere correctly to the peristomal region, thus allowing the aggressive body discharges to escape. It has been found that the pastes are perfectly compatible with the common adhesives, which stick perfectly thereto, and that the period of protection, which depends on the aggressiveness of the body discharges, can range from one day to more than eight days, it being possible for the remaining paste to be removed, before it is replaced, simply by washing with soapy water.

The invention also relates to the application of the abovementioned pastes as inert carriers and/or vehicles for substances or preparations having therapeutic activity and acting by slow diffusion for prolonged percutaneous treatment.

The invention is described in more concrete terms with reference to the examples below, which are purely illustrative and in no way limit the invention. In these examples, unless indicated otherwise, the amounts are expressed in parts by weight per 100 parts of the final paste, with the exception of the weight of preservatives which it may also contain.

EXAMPLE 1

(a) 3.3 parts of paraffin oil and 7 parts of water were added to 6 parts of the palmitostearate of glycerol and of polyoxyethylene glycol. The mixture was heated to a temperature of about 70° C. in order to produce an emulsion.

(b) 3 parts of sorbitol and then 0.05 parts of sorbic acid and 0.1 part of the sodium salt of methyl p-hydroxybenzoate were added separately to 2 parts of crosslinked and insolubilized polyvinylpyrrolidone.

(c) In a separate operation, 33 parts of demineralized water were added to 30 parts of polyvinylpyrrolidone of molecular weight 25,000, and the mixture was agitated until the polyvinylpyrrolidone had completely dissolved. At a temperature below 70° C., 8.8 parts of sodium alginate and then 7 parts of insolubilized carboxymethylcellulose were added, with agitation. Once this preparation was very homogenous, the temperature was kept below 70° C. and the products from steps a and b were added, with agitation. The agitation was continued for a further 15 minutes.

The paste obtained had the following composition:

|  | Parts by weight per 100 parts by weight of paste* |
|---|---|
| Crosslinked and insolubilized polyvinylpyrrolidone. | 2.0 |
| Polyvinylpyrrolidone of MW 25,000. | 30.0 |
| Insolubilized carboxymethylcellulose. | 7.0 |
| Sodium alginate. | 8.80 |
| Aqueous sorbitol | 3.0 |
| Paraffin oil | 3.20 |
| Palmitostearate of glycerol and of polyoxyethylene glycol | 6.0 |
| Demineralized water | 40.0 |

*without preservative.

A further 0.1 part of the sodium salt of methyl p-hydroxybenzoate and 0.05 part of sorbic acid were added as preservatives.

EXAMPLE 2

(a) 3.8 parts of paraffin oil were added to 7.1 parts of the palmitostearate of glycerol and of polyoxyethylene glycol. The mixture was heated to 70° C.

(b) 3.6 parts of sorbitol, 0.05 part of sorbic acid and 0.1 part of the sodium salt of methyl p-hydroxybenzoate were added separately to 2.3 parts of crosslinked and insolubilized polyvinylpyrrolidone.

(c) In a separate operation, 28.6 parts of demineralized water were added to 35.7 parts of polyvinylpyrrolidone of MW=25,000, with agitation, and 10.6 parts of sodium alginate, and 8.3 parts of insolubilized carboxymethylcellulose were then incorporated into this preparation, with agitation.

The product from step (b) was then added to this preparation, with agitation, the temperature being kept below 70° C., and the product from step (a) was added. The agitation was continued for a further 15 minutes.

The paste obtained had the following composition:

|  | Parts by weight per 100 parts by weight of paste* |
|---|---|
| Crosslinked and insolubilized polyvinylpyrrolidone. | 2.3 |
| Polyvinylpyrrolidone of MW 25,000. | 35.7 |
| Insolubilized carboxymethylcellulose. | 8.3 |
| Sodium alginate. | 10.6 |
| Aqueous sorbitol. | 3.6 |
| Paraffin oil. | 3.8 |
| Palmitostearate of glycerol and of polyoxyethylene glycol. | 7.1 |
| Demineralized water. | 28.6 |

*without preservative.

A further 0.1 part of the sodium salt of methyl p-hydroxybenzoate and 0.05 part of sorbic acid were added.

EXAMPLE 3

The procedure indicated in general terms in Example 1 was followed and a paste having the following composition was obtained, the respective proportions of the components used being those mentioned below.

|  | Parts by weight per 100 parts by weight of paste* |
|---|---|
| Crosslinked and insolubilized polyvinylpyrrolidone. | 2.0 |
| Polyvinylpyrrolidone of MW 25,000. | 30.0 |
| Insolubilized carboxymethylcellulose. | 10.0 |
| Sodium alginate. | 10.0 |
| Aqueous sorbitol. | 5.0 |
| Paraffin oil. | 5.0 |
| Palmitostearate of glycerol and of polyoxyethylene glycol. | 8.0 |
| Demineralized water. | 30.0 |

*without preservative.

A further 0.05 part of sorbic acid and 0.1 part of the sodium salt of methyl p-hydroxybenzoate were added.

EXAMPLES 4 to 13

The procedure indicated in Example 1 was followed, but the respective amounts of the components used were varied. With the exception of the possible presence of other additives, such as preservatives, pastes according to the invention were obtained which were all suitable for the purposes mentioned, the compositions of these pastes being recorded in Table I below.

The ratios of stearate/(water+oil+sorbitol) and PVP/water were calculated for each of these pastes and also for those of Examples 1 to 3; the values obtained are shown in Table II below.

TABLE I

| | Parts by weight per 100 parts by weight of paste | | | | | | | | | |
|---|---|---|---|---|---|---|---|---|---|---|
| | EXAMPLE | | | | | | | | | |
| | 4 | 5 | 6 | 7 | 8 | 9 | 10 | 11 | 12 | 13 |
| Crosslinked and insolubilized polyvinylpyrrolidone | 1.6 | 2.0 | 2.2 | 2.5 | 2.2 | 1.9 | 1.9 | 2.1 | 2.1 | 1.8 |
| Polyvinylpyrrolidone of MW 25,000 | 29.9 | 29.9 | 33.4 | 36.5 | 40.0 | 23.9 | 35.5 | 37.6 | 31.8 | 29.4 |
| Insolubilized carboxymethyl-cellulose | 7.0 | 7.0 | 7.8 | 8.2 | 10.0 | 19.1 | 11.8 | 10.0 | 9.5 | 8.8 |
| Sodium alginate | 2.8 | 8.8 | 9.8 | 10.7 | 10.3 | 19.1 | 11.8 | 10.0 | 11.0 | 10.3 |
| Aqueous sorbitol | 3.0 | 3.0 | 3.3 | 3.6 | 5.0 | 3.1 | 3.1 | 3.2 | 4.8 | 4.4 |
| Vaseline oil | 3.3 | 3.3 | 3.3 | 3.9 | 4.5 | 3.1 | 3.1 | 3.2 | 4.8 | 4.4 |
| Palmitostearate of glycerol and of polyoxyethylene glycol | 6.0 | 6.0 | 6.6 | 7.3 | 8.0 | 5.9 | 9.2 | 8.8 | 4.2 | 11.5 |
| Demineralized water | 46.4 | 40.0 | 3.4 | 27.3 | 20.0 | 23.9 | 23.6 | 25.1 | 31.8 | 29.4 |

TABLE II

| | EXAMPLE | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Powder/water | 1.45 | 1.91 | 1.67 | 0.86 | 1.14 | 1.53 | 2.03 | 3.075 | 2.50 | 2.50 | 2.30 | 1.65 | 1.65 |
| Stearate/ (water + oil + aqueous sorbitol) | 0.13 | 0.20 | 0.20 | 0.11 | 0.13 | 0.165 | 0.21 | 0.27 | 0.20 | 0.31 | 0.28 | 0.10 | 0.30 |
| PVP/water | 0.75 | 1.25 | 1.00 | 0.64 | 0.75 | 1.00 | 1.34 | 2.00 | 1.00 | 1.50 | 1.50 | 1.00 | 1.00 |

The pastes obtained had a more or less hard consistency, depending on the particular case, but they were all suitable for the purposes, indicated above, for which they are more especially intended.

I claim:

1. A skin-protecting composition which is in paste form and comprises (in effective amounts):
   (a) at least one hydrocolloid and/or another superabsorbent derived from hydrocolloids,
   (b) an insolubilized carboxymethylcellulose,
   (c) a polyvinylpyrrolidone having a molecular weight in the order of 25,000 to 30,000,
   (d) demineralized water,
   (e) an oil,
   (f) a stearate, and
   (g) a crosslinked and insolubilized polyvinylpyrrolidone.

2. A paste as claimed in claim 1, which also contains sorbitol and/or polyethylene glycol.

3. A paste as claimed in claim 2, wherein the crosslinked and insolubilized polyvinylpyrrolidone constitutes at most 3% by weight of the weight of the final paste.

4. A paste as claimed in claim 2, wherein the hydrocolloid contains an alkali-metal alginate.

5. A paste as claimed in claim 2, wherein the oil is a paraffin oil.

6. A paste as claimed in claim 2, wherein the oil is vaseline oil.

7. A paste as claimed in claim 2, wherein the stearate is a fatty alcohol stearate selected from the palmitostearate of glycerol and of polyoxyethylene glycol, the palmitostearate of ethylene glycol and of polyethylene glycol and the palmitostearate of glycols in combination with a polyoxyethyleneated fatty alcohol phosphate.

8. A paste as claimed in claim 1, wherein the paste comprises components in the following ratios and proportions by weight/weight:
   powder/water: 1 to 3 approximately,
   stearate/(water+oil+sorbitol and/or polyethyleneglycol) ≧ 0.10, and
   PVP/water: 0.5 to 2 approximately, the term "powder" denoting all pulverulent components together.

9. A paste as claimed in claim 1, wherein the crosslinked and insolubilized polyvinylpyrrolidone constitutes at most 3% by weight of the weight of the final paste.

10. A paste as claimed in claim 1, wherein the hydrocolloid contains an alkali metal alginate.

11. A paste as claimed in claim 1, wherein the oil is a paraffin oil.

12. A paste as claimed in claim 1, wherein the stearate is a fatty alcohol stearate chosen from amongst the palmitostearate of glycerol and of polyoxyethylene glycol, the palmitostearate of ethylene glycol and of polyethylene glycol and the palmistostearate of glycols in combination with a polyoxyethyleneated fatty alcohol phosphate.

13. A paste as claimed in claim 11, wherein the oil is vaseline oil.

14. A process for protecting skin against body discharges which comprises applying an effective amount of a paste as claimed in claim 1 to skin subject to attack by body discharges.

15. A process according to claim 14 wherein the skin is subject to attack by weeping wounds and/or by matter flowing out of stomata from the urinary or digestive tract.

16. A process for protecting skin against body discharges which comprises applying an effective amount of a paste as claimed in claim 2 to skin subject to attach by body discharges.

17. A process according to claim 16 wherein the skin is subject to attack by weeping wounds and/or by matter flowing out of stomata from the urinary or digestive tract.

18. A paste as claimed in claim 8 wherein the ratio of stearate/(water+oil+sorbitol and/or polyethylene glycol) is about 0.15.

19. A paste as claimed in claim 8 wherein the ratio of powder/water is from 1.5 to 1.9.

* * * * *